United States Patent [19]

Cohen

[11] 4,346,697

[45] Aug. 31, 1982

[54] METHOD FOR TREATING DEPRESSION AND OTHER MALADIES BY MEANS OF PATIENT-CREATED SYMPTOM GRAPHS

[76] Inventor: Kopel H. Cohen, 58 Kettle Creek Rd., Weston, Conn. 06880

[21] Appl. No.: 17,109

[22] Filed: Mar. 5, 1979

[51] Int. Cl.³ ............................................. A61B 19/00
[52] U.S. Cl. .................................. 128/1 R; 283/1 A; 128/630
[58] Field of Search ............... 283/1 A, 1 R; 128/1 R, 128/630; 35/17, 48 A, 48 R, 22 R, 24 R; 434/262

[56] References Cited

U.S. PATENT DOCUMENTS

| | | | |
|---|---|---|---|
| 1,526,717 | 2/1925 | Nunez | 283/1 R |
| 1,988,634 | 1/1935 | Stonecypher | 35/17 |
| 2,248,162 | 7/1941 | De Araujo | 128/630 |
| 2,622,899 | 12/1952 | Abrams | 283/1 R |
| 3,913,118 | 10/1975 | Abrams | 283/1 R |
| 3,951,062 | 4/1976 | Abramson | 283/1 A |

OTHER PUBLICATIONS

ECDEU Assessment Manual for Psychopharmacology, U.S. Dept. H.E.W., NIMH, Rockville, Md., 20852, Guy, 1976.
Research Diagnostic Criteria Second Edition, Spitzer et al., Biometrics Research, New York State Psychiatric Institute, N.Y., N.Y., 11/75.
Self Rating Depression Scale, Zung et al., Arch. Gen. Psychiatry, vol. 13, Dec. 1965.
A Self Rating Depression Scale, Zung, Arch. General Psychiatry, vol. 12, Jan. 1965.
"Comprehensive Textbook of Psychiatry", Freedman et al., Williams and Wilkins Co., Balt., Md., 1972.

*Primary Examiner*—Stephen C. Pellegrino
*Assistant Examiner*—J. L. Kruter

[57] ABSTRACT

The invention relates to a patient symptom chart on which symptom related graphs are created by the patient and a process of using these graphs in the treatment of various maladies including depression. Decision point plans or charts can also be used by the consulting physician in conjunction with the patient created graphs.

11 Claims, 6 Drawing Figures

DEPRESSION RECOVERY CHART   20

CODE:   NAME:   AGE:   SEX:   WEIGHT:   RECORD PERIOD / / TO / /

MEDICATION STARTED ON:   / /
                              DAY OF WEEK   DATE

YOUR MEDICATION IS: _____

THIS IS YOUR ANTIDEPRESSANT MEDICATION SCHEDULE.
PLEASE TAKE YOUR MEDICATION AT THESE TIMES 1  2  3  4  5  6  7  8  9  10  11  12  13  14
                             DATE DATE DATE DATE DATE DATE DATE DATE DATE DATE DATE DATE DATE DATE
                             23 21

1. YES, I TOOK MY ANTIDEPRESSANT MEDICATION
    AS SHOWN HERE.

2. MY MOOD TODAY:   30a   30
    HAPPY MOST OF THE TIME...
    HAPPY MORE THAN SAD OR BLUE...
    SAD OR BLUE MORE THAN HAPPY...
    SAD OR BLUE MOST OF THE TIME...
    SAD OR BLUE ALL THE TIME...
    SO SAD I COULDN'T STAND IT.

8. MY ENJOYMENT OF THE DAY:   30
    EVERYTHING WAS FUN...
    ENJOYED MOST OF THE DAY...
    FELT GOOD AT LEAST ONCE...
    TRIED TO STAY INVOLVED BUT HAD LITTLE ENJOYMENT...
    NOTHING WAS FUN THOUGH I TRIED TO STAY INVOLVED...
    AVOIDED ALL PEOPLE AND ACTIVITIES I USED TO ENJOY...

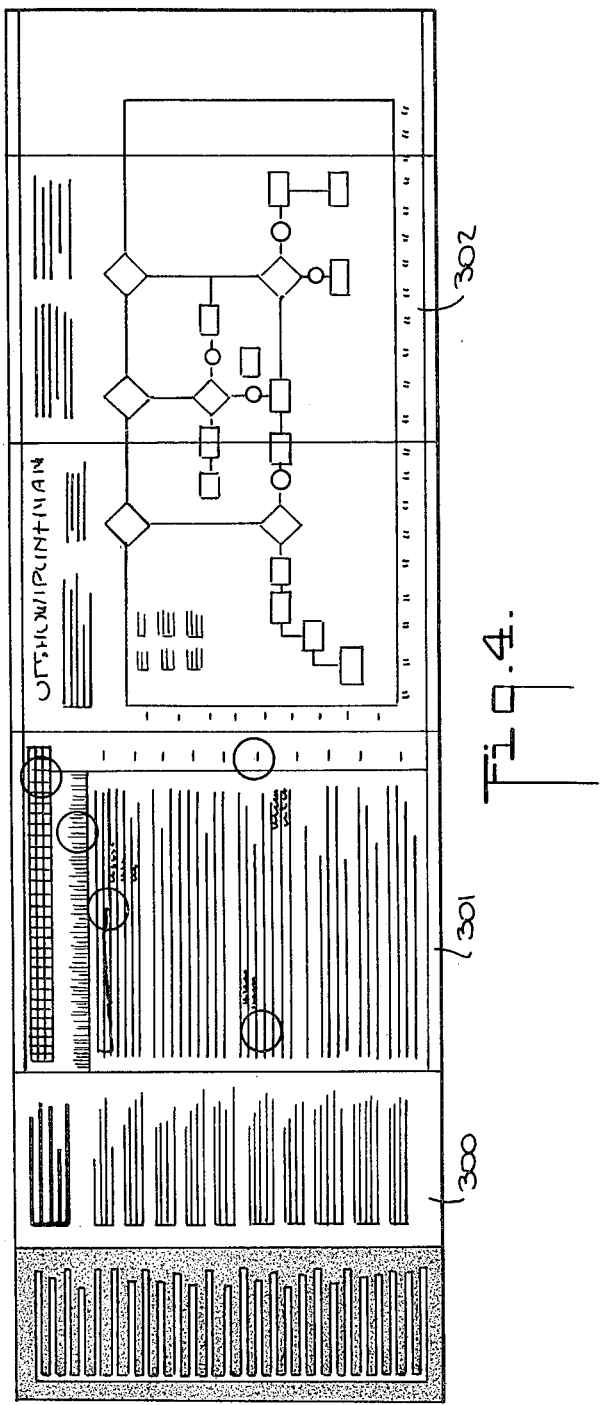
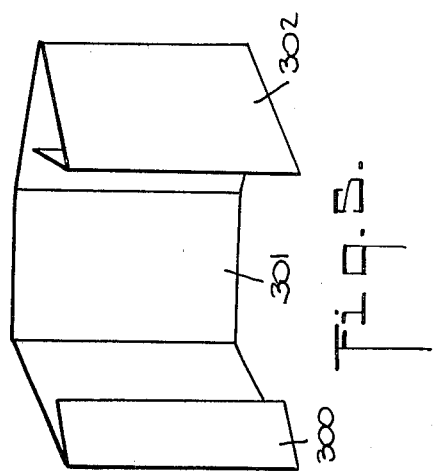
Fig. 4.
Fig. 5.

METHOD FOR TREATING DEPRESSION AND OTHER MALADIES BY MEANS OF PATIENT-CREATED SYMPTOM GRAPHS

This invention relates to a process of treating individuals afflicted by maladies and, in particular, by depression by means of symptom charts which are used in conjunction with the administration of medications. The invention also includes a decision point plan chart to be used by the physician in charge of the patient's treatment in interpreting and prescribing medication based on patient-created graphs.

According to a preferred embodiment of the invention, depression is treated by administering to the patient on a periodic basis, such as a daily basis, antidepression medication, such as a tricylic, the dosages of which will depend upon the patient's long-term reaction to the medication as indicated by the patient-created symptom graphs, which graphs are conveniently interpreted by the physician with the help of a decision point plan chart.

The patient is provided with a depression symptom chart which includes a plurality of symptom fields with each field corresponding to one particular symptom which is associated with depression, such as, for example, sleeplessness, loss of appetite, loss of energy, or inability to concentrate. Each of the symptom fields which relates to one of these symptoms would include a plurality of symptom indicatives arranged in a progressive series ranging from a symptom indicative relating to an extreme depressive state, through intermediate depressive states indicating improvement relative to the extreme state, up through a positive condition indicative which would generally correspond to the absence of depression. These symptom indicatives are arranged as one coordinate of a graph which is to be completed by the patient during this treatment period when he will be receiving medication. The other coordinate of the graph would correspond to the time period of treatment. Each day the patient would indicate on the graph the symptom indicative within each symptom field which most closely corresponds to his condition on that particular day. After a period of time there will be thereby created a graph of the patient's reaction to the medication. The fact that the graph is patient-created fosters a therapeutic alliance between the patient and the physician which can independently aid in the treatment of the patient in that the patient will participate actively in his treatment and this can improve ultimate patient progress.

The patient-created graphs are particularly suited to the treatment of depression, although, as will be mentioned, other maladies could be treated as well. The advantages of using the patient-created graphs in the treatment of depression are manifold and to appreciate these some background may be of use. In a typical case of depression, a patient may consult his family physician with some complaint such as inability to sleep, loss of energy, or a general feeling of hopelessness or worthlessness. The physician may check the patient for indications of various organic illnesses and it may be determined that the physician cannot identify the cause of the patient's complaint. The patient may, in fact, be suffering from depression which may be caused by a variety of factors, not all of them understood perfectly. One of these factors which can cause depression is considered to be a chemical imbalance in the patient's system which, in some cases, can be effectively treated by use of an antidepression medication, such as a tricylic. The physician, in considering the patient's symptoms, might consider prescribing a tricylic in order to determine whether or not the patient will respond positively to the medication. However, in the treatment of depression with a tricylic, there can be special problems caused by the fact that it can take several weeks for an improvement in the patient's condition to become perceptible as it is necessary for the tricylic to build up in the patient's system before positive results can be obtained. In the meantime, however, the patient may suffer from side effects from the tricylic with the result being that, for example, at the end of a few days' treatment, the patient may be feeling worse than he did before commencement of the tricylic treatment and stop taking the medication. Sometime after commencement of treatment, the patient will consult with his physician and the general physician-patient dialogue would take place wherein the physician would ask the patient if there has been any improvement. However, the changes in the patient's mood and feelings may be very subtle and difficult for the patient to identify as they occur in small increments on a day-to-day basis over an extended period of time. The side effects will also complicate matters as it can be unclear to the patient whether or not his condition has improved in view of the fact that side effects may lead the patient and the doctor to believe that there has been no improvement in the patient's depressive state while in fact there may have been such an improvement. The physician typically may pose to the patient very general questions such as "How are you feeling?" and the patient may respond very generally such as "Maybe better," which information will really not be useful in determining whether or not the patient is responding to the tricylic. In addition, if the physician were to engage in an extended interrogation of the patient in regard to various depression indicating symptoms such as mood, sleep, appetite, energy, guilt or enjoyment, in regard to an extended period of time such as two or three weeks and in regard to progressive improvement or lack thereof on a day-to-day basis, it would often be difficult for the physician to receive accurate information from the patient since it would be unlikely that the patient would be able to remember his relative particular feeling on each day of his treatment over this extended period of time. Further, given the realities of medical treatment, it is, in any event, unlikely that all general physicians would be prepared to spend the amount of time necessary to carry out a full interrogation of the patient so as to determine whether or not there has been perceptible improvement in regard to various symptoms over this extended period of time, particularly in view of the fact that it is unlikely that the patient would be able to provide this information. The net results of this can be that the family physician will hesitate to prescribe a tricylic in view of the difficulty in monitoring the patient's response to this medication, the time consuming nature of the treatment and the possible complications due to the side effects. Thus, the physician may refrain from exploring the possibility of treatment with tricylics and patients who could be effectively treated with tricylics may go without treatment.

By use of the patient-created graphs, these difficulties in the treatment of depressive patients can be reduced. In accordance with this invention, there is arranged a series of symptom indicatives with each series corresponding to a particular depression indicating symptom such as mood, sleep or appetite. The fact that the symptom indicatives are arranged to form a progressive series allows for the creation of a graph which can be interpreted quickly by the physician without spending undue time. That is, at a glance, the physician can determine whether or not the medication in question is having a positive effect on the patient as this will be reflected by an upward slope on the various graphs, and no lengthy day-by-day analysis of the patient's feelings within the series of days of treatment based on the doctor's interrogation of the patient is necessary during the patient's consultation time with the physician.

The patient-created graphs should in no way be considered to be a substitute for physician-patient dialogue. On the contrary, these dialogues would still take place but would be made more meaningful since they would be based on more accurate symptom information as reflected in the symptom graphs, which are created daily by the patient in regard to predetermined symptoms. The physical format of the progressive series of symptom indicatives ranging from extreme symptom to absence of depressive symptom will mean that the patient-created charts can be analyzed by the physician at a glance and that needless physician analysis of symptom data can be eliminated. The fact that the graphs are patient-created means that information which would otherwise be lost by reason of the patient's inability to recall subtle changes on a day-to-day basis is maintained and the fact that this information can be quickly assimilated by the doctor means that doctors will not be deterred from exploring the possibility of treatment for antidepression and will allow the physician-patient dialogue to be focused on more substantive issues of patient treatment.

Furthermore, the fact that symptom indicatives are preprinted and need not be independently determined by each physician allows a considerable time saving on the part of each physician and provides for the possibility of obtaining a uniform data base in that a large number of patients can be studied in terms of their reactions to medication described with the same symptom indicatives. This allows for the amassing of useful clinical data whereby large numbers of patient-completed graphs could be analyzed by scientists so that physicians can be advised as to the accumulated experience of their fellow physicians. Such large scale analysis could lead to substantial progress in the understanding and treatment of the malady. Further, these uniform records could be of use in regard to governmental or private monitoring of certain drugs or treatment methods in order to determine whether a particular drug is effective for purposes indicated and does not pose untoward dangers.

The benefits of treatment processes using the patient-created graphs having standardized symptom indicatives are at least as follows:

The individual patient is treated in an optimum fashion in that there is an accurate record of the patient's day-to-day reactions to the medication, which reactions are set forth in a form which can be quickly assimilated and analyzed by the physician in charge. There will be no loss of important patient response information because of the inability to recall occasioned by the passage of time and because of possible physician unwillingness to devote substantial time to detailed patient interrogation.

The participation of the patient allows for a therapeutic alliance between patient and physician which can be of aid to the patient in that the patient becomes an active partner in his treatment. Thus, the fact that the patient is making the charts constitutes in and of itself a factor in the treatment of the patient.

Furthermore, because of the nature of depression, the mere existence of the charts can provide an important thereapeutic support for the patient. This is due to the fact that an individual who commences to experience the symptoms of depression, such as lack of ability to think and make decisions, may believe that he is verging on insanity, which belief could independently have a traumatic psychological impact. When the patient sees a preprinted chart, which is used in connection with a medication, the patient will realize that others suffer the same symptoms, that the patient is not an isolated case, and that medication is appropriate to treatment as in the case of more familiar organic illnesses. Thus, the mere existence of the preprinted charts constitutes a positive factor in the patient's treatment.

Since the patient does participate in the creation of his own record of treatment, the physician saves time thereby allowing him to utilize his talents in a more effective manner in the treatment of the patient.

The charts will complement and make more useful these physician-patient discussions which would, in any event, take place.

Since the symptom indicatives are standardized, the patient-created graphs can be collected and analyzed on a large scale so that the collective experience of a large number of physicians can be rendered accessible. This collective experience, which would otherwise be lost, could conceivably lead to fundamental progress in the future treatment of depression.

Again, since these records are standardized and can be easily and conveniently collected, it becomes possible to monitor the effect of certain drugs or treatment methods on a large scale basis in order to determine whether a particular drug is effective for the purposes intended and not dangerous. Such monitoring could be an effective aid in safeguarding the public in regard to ineffective or dangerous drugs.

The invention also contemplates the use of a decision point plan chart to be used by the doctor in conjunction with the patient-created symptom graphs and the prescribed medication. The decision point plan chart can be used by the physician to follow easily the various stages of the patient's treatment. The point plan chart indicates to the physician the amount of time that a patient should be administered a particular medication, and the dosage to be administered, based on the patient's reaction thereto as set forth in the patient-created symptom graphs. The decision point plan chart allows for uniformity of treatment of patients in accordance with treatment methods which are set forth on the basis of experience beyond that which normally could be amassed by any particular physician in a general practice. The uniformity of treatment method assured by the decision point plan chart reinforces the above-discussed advantage relating to the amassing of data on a large scale basis in that a data base can be obtained which will be susceptible of analysis because of the uniformity of the principles used in the creation of the data base.

Although the particular embodiments of the invention described hereinafter are in regard to the treatment of depressive patients by means of the controlled administration of anti-depressive drugs, it is clear that the invention would find wider application. Areas in which the techniques taught by this invention would be of use would be in regard to those maladies which require a periodic administration of medication and the monitoring of the patient's reaction thereto, with this monitoring being in regard to symptoms which the patient, or those around him, such as the patient's family, would be capable of assessing. Further, those maladies, the treatment of which could be aided by means of the creation of a therapeutic alliance between the physician and the patient, would also be advantageously treated by means of the symptom charts according to this invention. Examples of maladies which could conceivably be treated by use of symptom graphs would be arthritis, hypertension, anxiety, perinatalogy, weight control, migrane, or juvenile depression, which latter might be treated by means of graphs created by the juvenile's parents. Of course, other maladies could also be susceptible to treatment by means of the symptom charts.

FIG. 1 shows the patient's copy of the depression symptom chart.

FIGS. 4 and 5 depict a doctor's version of the depression treatment kit.

FIG. 1 shows the patient's copy of the depression symptom chart. As seen in FIG. 1, the chart includes an identifying indicia such as the patient's name, age, sex and weight, an identifying code, an indication of the date on which medication started and the time period to which the chart applies.

Figure 2:
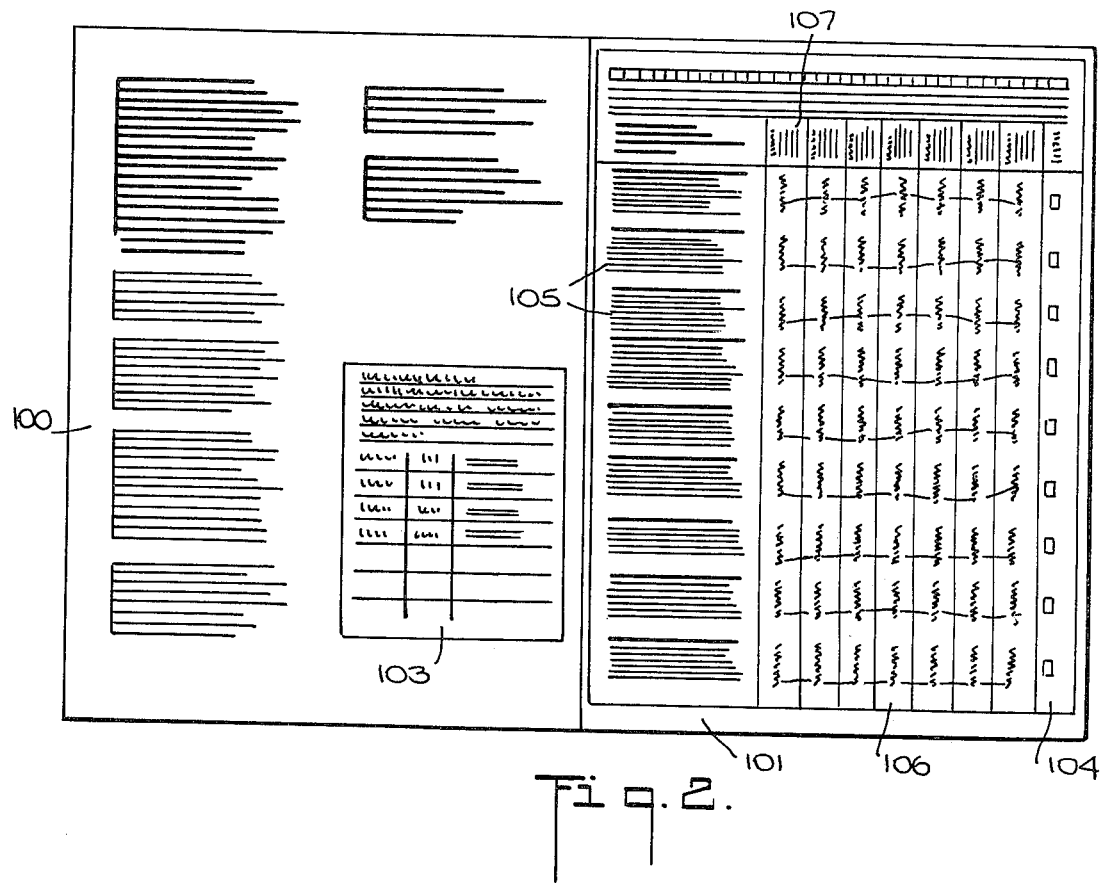
FIG. 2 shows a 7 or 14 day patient folder for the symptom chart and patient instructions.

The next field on the depression symptom chart is the antidepressant medication schedule field 21 which includes a blank field for receiving the physician's indication of the medication to be self-administered by the patient and includes a plurality of date columns 23 corresponding to the days on which the medication is to be taken, with the quantities of the medication to be taken being entered into date columns 23. The physician completed date columns provide a convenient manner of indicating to the patient the quantity of medication to be administered on any given day. The medication can be taken by the patient in dosages staggered at various times throughout the day or at a single time each day depending on the patient's reactions, schedule or other factors which the physician may consider relevant and time scheduling within a day can also be listed by the physician adjacent the date columns 23. Although it is not shown in the drawing, there would be instructions that the patient place an X over those dosages which the patient has actually self-administered. This will provide a check that the patient has actually followed instructions as to dosage.

The symptom chart next includes a series of seven symptom fields 30 numbered 2-8 with only symptom fields 2 and 8 shown in FIG. 1. The series of symptom fields 30 preferably consists of a series of symptom indicatives 30a which are arranged in a progressive series ranging from an extreme depressive state indicative, through intermediate depressive state indicatives, which indicate improvement relative to the extreme indicative, to a positive condition indicative which would generally indicate absence of depression. For example, a first symptom key question is "My mood today?" The symptom indicatives 30a range from the extreme depressive state "So sad I couldn't stand it" up through a graduated sequence of intermediate depressive indicatives such as "Sad or blue all of the time," followed by "Sad or blue most of the time," followed by "Sad or blue more than happy," followed by "Happy more than sad or blue." Finally, the uppermost symptom indicative would be a relatively positive condition symptom such as "Happy most of the time."

In the above example, the symptom key question focusing on mood is associated with a graduated sequence of symptom indicatives 30a which range from despondent through almost euphoric with the progression between each indicative of the series being as uniform as is possible within the limits of the English language.

According to a preferred embodiment, the symptom key questions and their related graduated series of symptom indicatives would be as follows:

2. My mood today:
   Happy most of the time
   Happy more than sad or blue
   Sad or blue more than happy
   Sad or blue most of the time
   Sad or blue all of the time
   So sad I couldn't stand it
3. My sleep last night:
   Slept really well and awoke rested
   Slept all night but woke up tired
   Awoke but went back to sleep
   Slept without waking but awoke very early
   Awoke and couldn't go back to sleep
   - - - - - -
   Slept too much
4. My appetite today:
   Ate normally and enjoyed it
   Ate less but enjoyed it
   Ate normally but didn't enjoy it
   Ate less and didn't enjoy it
   Ate very little
   Didn't eat anything
   - - - - - -
   Ate too much
5. My energy today:
   Great energy
   Normal energy
   Less than normal energy
   Tired easily
   Drained of energy all day
   Too tired to move
6. My ability to think and make decisions:
   Mentally sharp all day
   Mentally dull at times
   Mentally dull but could function
   Mental dullness interfered with function
   Could barely function
   So mentally dull I couldn't do anything
7. My ability to carry on today?
   On top of everything
   Did as well as most people
   Tried my best but things went wrong
   Disappointed in my mistakes
   Blamed myself for everything wrong
   Sure things will never improve
8. My enjoyment of the day:
   Everything was fun
   Enjoyed most of the day
   Felt good at least once
   Tried to say involved but had little enjoyment Nothing was fun though I tried to stay involved
Avoided all people and activities I used to enjoy
9. My symptoms today: (note any symptom you noticed.)
Fell down
Felt faint
Unsteady walking
Trouble urinating
Constipation
Blurred vision
Dry mouth
Hand tremor
Sleepiness
Excessive sweating
Poor memory It is seen from the above listing that there are seven symptom fields numbered 2 through 8 with each symptom field corresponding to a different symptom which is generally associated with depression. The last symptom field, field 9, is not arranged in the form of a graduated series of symptom indicatives relating to one particular symptom as is the case with fields 2 through 8. Symptom field 9 is a simple listing of possible side effects with each of these individual side effects being listed individually. Symptom field 9 does not convey its information in the form of a graph to the examining physician but rather in terms of a yes, no response for each particular day and in regard to each particular side effect.

Each of the symptom fields 2 through 8 corresponds to one particular depression-associated symptom: field 2 corresponds to mood, field 3 corresponds to sleep, field 4 corresponds to appetite, field 5 corresponds to energy, field 6 corresponds to thought, field 7 corresponds to guilt/outlook, and field 8 corresponds to enjoyment.

Other symptom key questions and symptom indicatives could, of course, be provided.

What is sought in regard to the symptom indicatives is a series of symptom descriptive declarations wherein a reasonably uniform progression in symptom intensity ranging from an extreme depressive symptom up through a positive condition symptom is set forth. Of course, due to the limits of language, the symptom indicatives can not always be kept in precisely limited definitional compartments and the indicatives considered in isolation could conceivably be construed as having some overlap such as the indicatives "Too tired to move" and "Drained of energy all day," but, in general, the indicatives show a uniform progression. In addition, the very physical arrangement of the indicatives from extreme depressive symptom up through positive condition symptom will, in an of itself, aid in making more definite the meaning of the indicatives. That is, if a patient one day identifies the symptom indicative "Tired easily" in regard to the symptom key question "My energy today?" and the next day felt tired but did feel some improvement from the previous day, the patient would normally check the next symptom indicative in the progression, "Less than my normal energy." Thus, the very arrangement of the indicatives suggests to the patient the shades of meaning and helps insure that the important information, the patient's relative progress, will be ultimately communicated to the physician.

Arranged adjacent to the symptom indicatives is a matrix of patient markable zones 41 including a series of date columns 40, with each of said columns corresponding to a sequential date in the patient's treatment schedule. The patient markable zones 41 are arranged in rows corresponding to particular symptom indicatives and in columns corresponding to a particular date. The entire matrix field of patient markable zones 41 constitutes, therefore, a patient markable graph which will be completed by the patient himself as the patient progresses through his treatment. A patient may begin treatment checking the markable zone regarding mood corresponding to "So sad I couldn't stand it" for a period of a week or more until the anti-depressant medication has built sufficiently in the patient's blood stream to change the patient's mood so that the patient can check the zone corresponding to "Sad or blue all of the time" and up through the other symptom indicatives related to the mood symptom key question. After a period of time, for example, the patient may have progressed up through "Happy more than sad or blue" and, with the patient markable zone appropriately marked, the zone will constitute a graph showing an upward trend indicating the patient's progress to the patient and his physician. Thus, it is the patient himself who completes his symptom progress graph by completing the patient markable zones each day of his treatment with the result that the patient becomes an active participant in his treatment and obtains additional reinforcement in the form of his graphical contribution to his treatment.

It is seen, therefore, that there will be created a plurality of patient marked graphs indicating the patient's progress or lack thereof with the graphical indications being referenced to preprinted symptom indicatives arranged as one coordinate of the patient markable graph with treatment dates being the other coordinate of the graph. When each graph is completed by means of the patient filling in the matrix adjacent the symptom indicatives, there will be created an accurate, easy to interpret indication of whether or not the patient is responding to the anti-depressant medication on a long term basis.

It is contemplated that the symptom chart be provided in four copies, the top copy would be preserved by the patient as this would be consistent with the patient participation therapeutic alliance concept whereby the patient is assuming an active role in his treatment. The second and third copies are intended for the treating physician and would be substantially similar to the patient's copy except that there would be superimposed over each of the symptom fields a single word indicative of the symptom in that particular field. For example, field 2 would have the word "mood" superimposed in large print over the symptom indicatives, but printed in such a way so that the symptom indicatives can be read through the superimposed key word. The superimposed, relatively largely printed key words for fields, 2 through 8, which would appear on the physician's copies of the charts would be: field 2—"mood", field 3—"sleep", field 4—"appetite", field 5—"energy", field 6—"thought", field 7—"guilt/outlook", field 8—"enjoyment". Thus, when the physician receives his two copies of the patient's completed drafts, he will see at a glance the relatively large superimposed key words, mood, sleep, appetite, energy, etc., and adjacent to these key words the patient-created graph showing whether or not there has been relative progress in regard to this particular symptom. If the physician wishes to consider in detail each of the symptom indicatives, he can, of course, read these indicatives through the the superimposed overprinted key term but the important information, relative progress in regard to each of the general symptoms, can be assimilated by the physician at a glance.

As mentioned, the physician will receive two copies of the patient-completed graphs. The one copy of the graphs which the physician receives can be useful in regard to those situations where the physician is consulting with a specialist in the field. In some situations the physician may feel it advisable to work with the specialist in treating a particular patient and it would be a simple matter for the physician to mail the second copy of the patient-created graph which was given to him by the patient to the consulting physician and to discuss the results with the consultant, perhaps by telephone.

The fact that the symptom indicatives are preprinted and need not be independently determined by each physician is significant since the time saving to the physician is substantial. Since the symptom indicatives would be meaningful in regard to large numbers of depressive patients, there will be achieved a net time savings by using the preprinted indicatives and patient-created graphs which allows the physician to treat economically patients who might otherwise go without treatment and to spend his time in considering other matters which are not susceptible to systemization. Furthermore, the physician will be able to accumulate a library of completed patient marked graphs showing the correspondence between progress, dosage, and medication which will allow the physician to reach his own conclusions as to effective treatment of future patients. As mentioned above, it is contemplated that there be four copies of the patient-created graphs, one for the patient, two for the physician and the fourth graph, which would not bear the patient's name in order to preserve confidentiality, could be sent to a central processing center where large numbers of the patient-completed graphs could be analyzed so that physicians can be advised as to the accumulated experience of their fellow physicians which could possibly lead to substantial progress in the future treatment of the malady. Further, the records could be of use in regard to possible private or government monitoring of certain drugs or treatment methods in that the information on the symptom charts could indicate whether a particular drug is effective for purposes intended or possibly dangerous. Of course, in regard to this fourth copy intended for mass processing, it would be necessary to obtain the patient's consent for this purpose, even though the patient's name would not appear on the fourth copy. Should the patient not wish to consent to have his graphs included for central analysis, the fourth copy would not be used and could be discarded by the physician.

When the patient does meet with the physician, the physician will have an accurate record of the patient's progress as shown by the patient-marked graph with the patient's progress in regard to symptom indicatives and dates being readily observable. The advantages in regard to such a patient-completed chart covering an extended period of time would be evident as it would be otherwise difficult for a patient to recall all or even any of his particular symptoms or a particular day and any relevant improvement over a previous day.

Thus, a key aspect of the invention is the fact that, with the charts, it becomes possible to obtain an accurate record of the patient's response to the anti-depressant medication which will permit effective monitoring and dosage alteration. Without the charts, a patient consulting with his physician would be placed in a position of attempting to recall his various feelings on each particular day of an extended period in regard to a variety of symptoms which would be, for all practical purposes, impossible. Furthermore, it is likely that many physicians would not feel that complete interrogation of the patient in regard to his feelings over an extended period of time would be practical and that physician time could be better spent if directed elsewhere. The net result of this would be that, without the graphs, there would in many cases be no effective monitoring of the patient's response to the anti-depression drugs because of impracticality.

As mentioned, the patient-created graphs are in no sense a substitute for physician-patient personal contact. The graphs make the physician-patient personal contact more useful. The charts will allow the physician-patient dialogue to continue but this dialogue will be targeted on more substantive issues of treatment and will leave issues such as amount and regularity of medication and the patient's feelings on each particular day of the treatment to be dealt with by the chart entries made when the patient's memory is fresh.

The patient markable graph is relatively simple for the patient to use since it does not, for example, require that the patient independently write out how he is feeling on a particular day or how his appetite, energy, and so forth, were on a particular day. If the patient markable graph shows no progress over a period of time, the physician will know that an increase in the dosage may be in order or that a change in medication should be considered. If the chart shows patient reaction which appears difficult to interpret or unusual, this could indicate to the physician that special problems exist.

FIG. 2 shows a 7-day patient folder in an opened position. Of course, other time periods covered by the chart could be included, such as a 14-day chart which would merely include additional date columns. The folder could be, for example, a simple plastic covered article which the doctor would give to the patient when starting the anti-depression treatment. The folder includes two pads 100 and 101 with the left hand half 100 containing permanent instructions. These permanent instructions will include information which would be disigned to improve patient cooperation and could, for example, generally indicate to the patient the nature of depression and the treatment which the patient is undergoing. Also on the left hand side of the folder in the lower right hand corner is the pocket 103 for a removable appointment/dosage card. On the right hand side 101 of the folder is clipped the depression symptom chart 104 which includes the aforedescribed symptom indicatives 105 and the patient markable graphs 106, each of which could include a matrix of patient markable zones such as discussed in connection with FIG. 1. The date columns 107 are seen at the upper portion of the chart and it will be noted that 7 date columns, corresponding to a one-week treatment, are provided in this particular embodiment.

As mentioned, the permanent instructions and information for the patient, which would preferably appear on the left hand side of the folder seen in FIG. 2, are selected so as to induce patient cooperation. There is preferably set forth information to the effect that the depression symptom chart is designed to help the patient keep track of his improvement while being treated for depression. The patient is informed that the doctor has diagnosed the patient's problem as depression which is a curable mental illness and that common symptoms of depression would be feeling sad or blue, trouble sleeping or waking up very early, lack of appetite, feeling drained of energy, having trouble concentrating and making decisions, feeling at fault, and/or feeling that nothing is any fun anymore. The patient would be informed that he may have just a few of these symptoms or all of them. The causes of depression can be set forth in layman's terms and the patient would be informed that depression can be cured if the patient makes an honest report of his symptoms so that the doctor can find the proper amount of medication for the patient. The patient will be directed to take his pills every day as instructed because, in order to be effective against depression, the medicine must build up in the patient's blood stream and that it may take two to four weeks before an effective quantity of the drug gets into the patient's blood stream. The patient is admonished that he should, therefore, take the medication every day in order to maintain drug buildup. Finally, the patient is informed that the medication is not habit forming, and that some physical side reactions to the anti-depressant are possible. Finally, the patient is informed that the chart is both for the patient and the doctor and that the patient's daily record will allow the patient to help himself feel better as well as help the doctor help the patient.

The physical proximity of the patient's permanent instructions and information in the left hand side of the patient's folder directly opposite the patient's self-markable graph can be advantageous in that the patient will be exposed to those instructions daily when the patient marks his graphs. The patient would, therefore, less easily lose sight of the importance of the medication and the symptom graphs to the treatment of the patient's depression. Use of the graphs also repetitively exposes the depressive patient to the permanent instructions which, in turn, help induce the patient continue using the graphs and medication.

Figure 6:
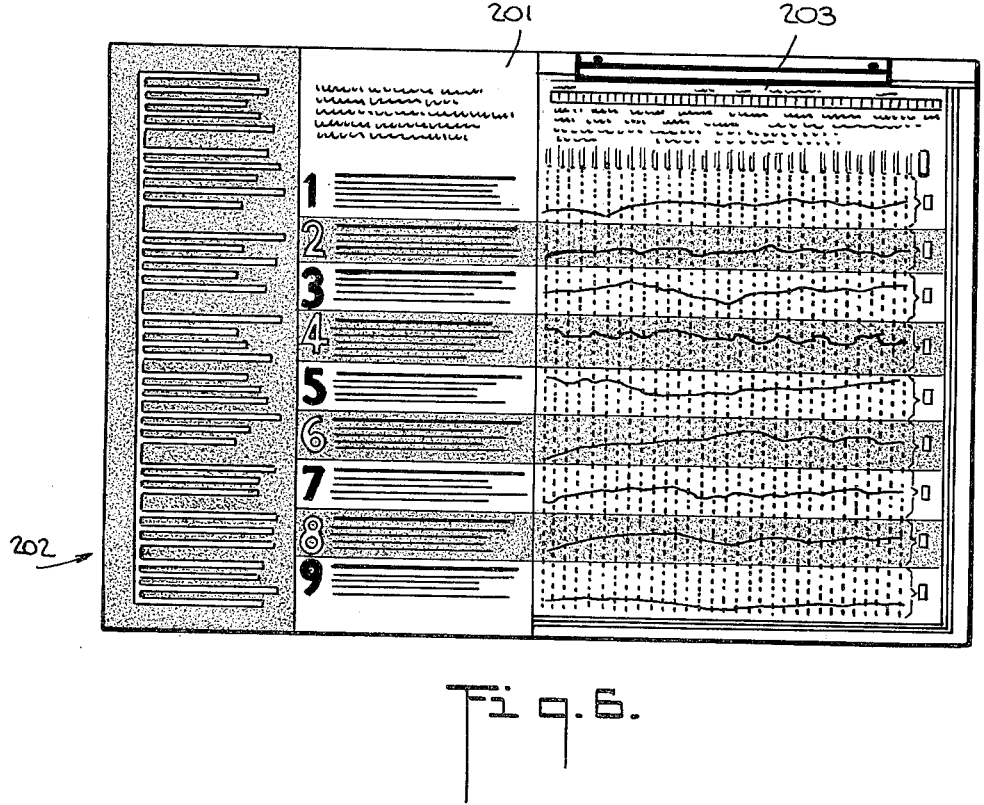
FIG. 6 shows a variation of the patient folder adapted for a 31-day period.

FIG. 6 shows a variation of the patient folder adapted for a 31-day period. The 31-day version of the patient folder is similar to the 7-day version discussed above in connection with FIGS. 1 and 2 except that the symptom indicatives are located, as is seen in FIG. 6, on the left hand side of the patient folder at 201 together with patient instructions at 202. The transposition of the symptom indicatives to the left hand side of the folder is effected so that the patient created graphs 203 can be made physically longer so as to cover the more extended 31-day treatment on a single graph field.

Figure 3:
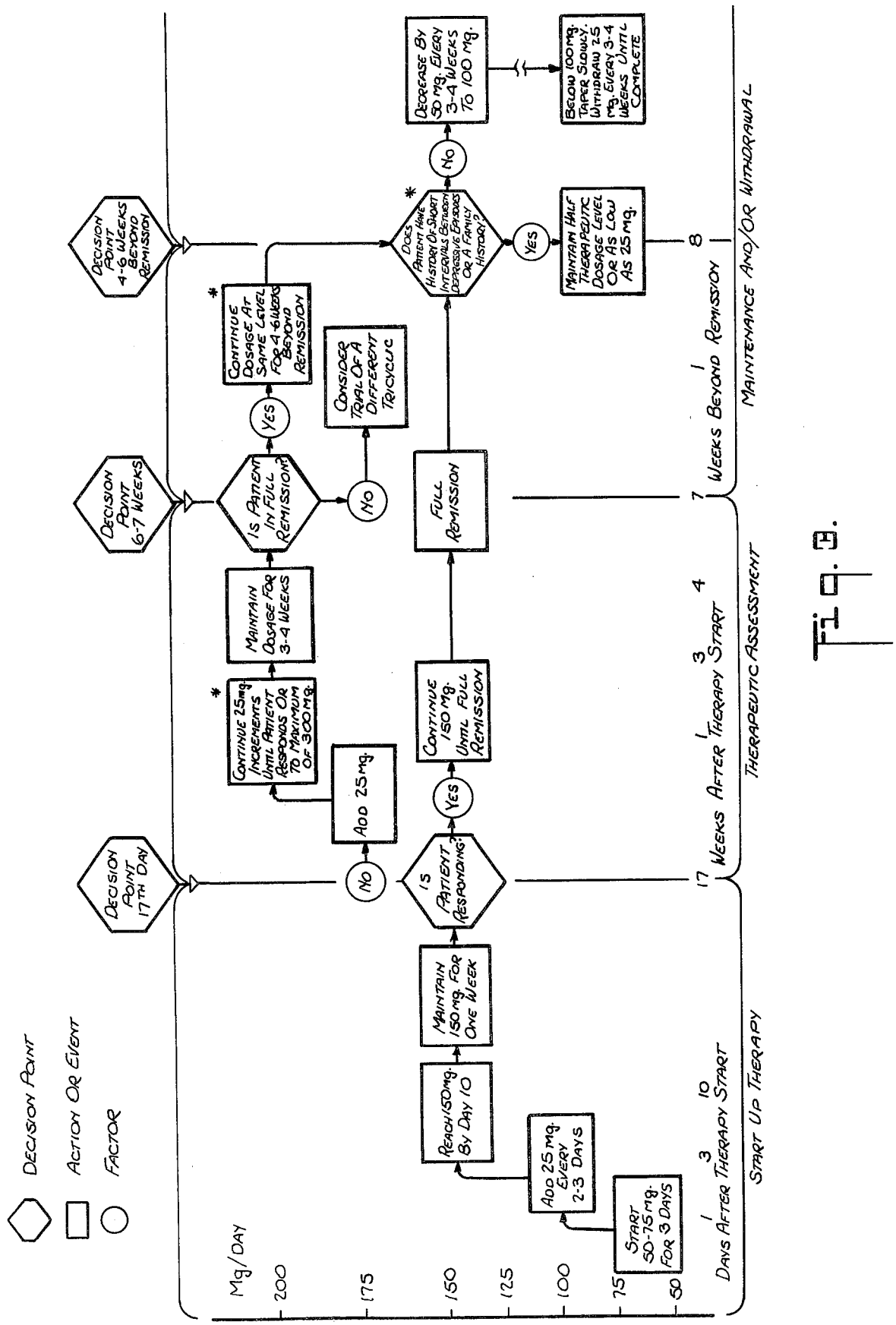
FIG. 3 shows a decision point plan chart to be used by the physician in conjunction with the patient-created symptom graph.

FIG. 3 shows a decision point plan chart for the treatment of depression which would be used by the physician in conjunction with the patient-created symptom graphs. The decision point plan is in graphical form as is seen in FIG. 3 which allows the physician to follow easily the various stages of the patient treatment. It is seen that the vertical coordinate of the physician chart seen in FIG. 3 is scaled in milligrams of a particular antidepressant medication, for example, Norpramine. The horizontal coordinate of the physician chart is scaled as to time phases of the treatment schedule. Starting at the lower left hand corner of the physician chart at day 1, it is seen that the physician is instructed to start the medication dosage at 50-75 mg for three days and, that 25 mg increases in dosage are to be made every 2 or 3 days until the dosage of 150 mg is reached by day 10. This 150 mg dosage is maintained for one week with the first decision point day occurring at the 17th day of treatment, as indicated on the FIG. 3 physician's point plan.

At day 17, the physician is to decide whether or not the patient is responding to the treatment. It is at this point that the patient created graphs described above in connection with FIGS. 1 and 2 become critical in determining the course of the patient's future treatment. The graphs are analyzed by the physician and indicate whether or not there has been an improvement in the patient's depressive state in terms of the predetermined symptom indicatives listed on the patient's symptom graphs. Such improvement is easy to determine since there will be an upward tend to the graphs if the patient is positively responding. The doctor, in considering the patient's graphs, can quickly, efficiently, and without an undue expenditure of consultation time, determine whether the patient has been complying with his medication instructions as set forth in the patient's depression treatment kit and, almost at a glance, the physician will be able to determine whether there has been an improvement in the patient's condition. If there has been an improvement, the physician would follow the "yes" branch at the 17th day decision point and would, therefore, as indicated on the physician chart, continue the 150 mg treatment until full remission has been achieved. If, on the other hand, the patient-created graphs indicate no response on the part of the patient, the physician would follow the "no" branch at the 17th day decision point and would, accordingly, add 25 mg to the patient's dosage every three days with such 25 mg increase continuing until the patient starts to respond to the medication or until a maximum dosage of 300 mg per day has been reached. As seen in the chart, the determined dosage will be maintained for three to four weeks and bring the doctor to his second decision point, located at the six to seven week treatment phase. At this second decision point the physician must decide whether the patient is in full remission and, again, this would be determined by a consideration of the patient-created symptom graphs. If the patient graphs indicate that the patient still is not responding to treatment, the physician would consider the use of a different tricyclic or other medication. On the other hand, if the patient is in full remission, the physician is instructed to continue dosage at the same level for four to eight weeks beyond remission until reaching the final decision point which is four to eight weeks beyond full remission. At this final point, the physician would determine whether the patient has a history of short intervals between depressive episodes and, if this is the case, the physician would maintain dosage at one-half the therapeutic dosage level or as low as 25 mg. If the patient has no history of intervals between depressive episodes, the physician would decrease the dosage by 50 mg every three or four weeks until the 100 mg level is reached and this would be maintained through the twelfth week beyond remission. At this point, at the twelfth week limit, the medication would be withdrawn at a rate of 25 mg every three or four weeks until no further medication would be administered.

It is contemplated that the decision point plan be incorporated into a doctor's version of the depressin treatment kit such as indicated in FIGS. 4 and 5. The far left panel 300, seen in FIGS. 4 and 5, preferably would include information concerning the depression treatment plan including information on side effects and would include an analysis of a completed sample patient symptom graph which would be included in the second panel 301. The use of sample symptom graphs in conjunction with explanatory commentary in the doctor's kit would be an effective and time-saving method of instructing the doctor in the use of the depression kit and patient prepared graphs. The full dosage chart is seen at 302 in FIGS. 4 and 5 and would include the information above discussed in connection with FIG. 3.

What is claimed:

1. A method for treating patients suffering from depression by means of the controlled administration of antidepressant medication comprising the steps of:
   a. administering to a patient suffering from depression an antidepressant drug on a daily basis for a first dosage period set by the practitioner, and in conjunction with the administration of said antidepressant drug during said first dosage period;
   b. administering to said patient suffering from depression a patient-completable symptom chart comprising a plurality of symptom fields, each symptom field corresponding to a particular symptom of depression, and
   c. said symptom fields being arranged sequentially on said chart, and
   d. each of said symptom fields including a series of printed symptom indicatives, with said symptom indicatives each corresponding to a particular degree of a related symptom and said symptom field including symptom indicatives ranging from an extreme manifestation of the symptom, to symptom indicatives indicating improvement in patient condition relative to said extreme symptom, to a positive symptom indicative indicating minimum manifestation of said symptom, and
   e. said symptom indicatives being arranged in said symptom field in a progressive sequence with the indicative relating to said extreme manifestation being at one end of said sequence, symptoms indicating improvement in said patient condition following said extreme symptom in said progressive sequence and said positive symptom being located at the other extremity of said progressive sequence, and
   f. a patient-markable graph field arranged in association with each of said symptom fields on said patient-completable symptom chart; said graph field including a series of columns with the number of said columns in said graph field being at least equal to the number of days covered by said first dosage period, and
   g. each of said columns including zone means for receiving a patient-applied indication, with each of said printed symptom indicatives having a zone means in correspondence therewith in each column of said graph field, and
   h. said patient assesses his symptoms during said first dosage period by the step of applying an indication in said zone means which corresponds to the symptom indicative most closely corresponding to said patient's assessment of his symptoms on each treatment date over said first dosage period, said patient thereby creating a graphical representation of said patient's symptoms on said symptom chart; and
   i. wherein upon the completion of said first dosage period, on the basis of said practitioner's assessment of the graph created on said symptom chart by said patient during said first dosage period, said practitioner increases the originally administered dosage of antidepressant drug to be taken by said patient or said practitioner maintains said dosage of antidepressant drug to be taken by said patient at said originally administered dosage level, said dosage of said antidepressant drug being increased when said patient-created graph shows no improvement in said symptoms associated with said patient's depression, and said dosage of antidepressant drug being maintained at said originally administered level when the slope of the line on said patient-markable graph field is upward or shows improvement in said symptoms associated with said patient's depression;
   j. the administration of said patient-completable chart in combination with said antidepressant drug providing a positive therapeutic effect.

2. The method according to claim 1 wherein said antidepressant medication is a tricyclic antidepressant drug.

3. The method according to claim 1 wherein said symptom chart further includes a medication schedule field comprising a plurality of columns with each of said columns being associated with date indicia and antidepressant medication dosage indicia, and each of said medication schedule field columns being aligned with said patient-markable graph field columns; and in further association with said medication schedule field columns, patient-markable zone for receiving an indication of the medication self-administered by said patient on said treatment date.

4. The method according to claims 1, 2 or 3 wherein said patient-mrkable graph field at the end of said first dosage period indicates improvement short of complete remission in said symptoms of depression, then said dosage of antidepressant medication administered during said first dosage period is administered for a second dosage period in combination with said patient-completable symptom chart having said graph field columns for each date of said second dosage period, said second dosage period continuing until said graph on said patient-completable symptom chart indicates that said patient suffering from depression is in full remission from said symptoms of depression, and thereafter said patient is maintained on said antidepressant drug for a third dosage period.

5. The method according to claims 1, 2 or 3 wherein at the end of said first dosage period said patient-completable chart indicates no improvement in patient symptoms, then over a second dosage period the dosage of said andidepressant medication is progressively increased by incremental amounts above the dosage administered during said first dosage period, and in combination therewith said patient-completable symptom chart is administered to said patient having a graph field column for each date of said second dosage period, said antidepressant medication dosage being progressively increased during said second dosage period until said graph on said patient-completable symptom chart indicates that said patient is responding to said antidepressant medication, said medication dosage level producing said response during said second dosage period is continued during a third dosage period until said patient is in full remission from said symptoms of depression, and thereafter said patient is maintained on said antidepressant medication.

6. The method according to claim 4 wherein during a final dosage period said maintenance dosage of antidepressant medication is gradually reduced until said patient is withdrawn from medication, wherein said patient does not have a family history of depression or a history of short intervals between depressive disorders.

7. The method according to climas 1 or 2 wherein each patient is treated under the direction of a treating practitioner and wherein a plurality of patients are treated by a plurality of practitioners in accordance with the metod of claims 1 or 2, wherein each of said patient-completable graphs upon being completed by the patients who have been treated, are collected and the data therefrom compiled, said compilation providing an indication of the responses of said plurality of patients to said treatment.

8. The method according to claims 1 or 2 wherein said symptom field comprises the symptom which is mood and the progressive sequence of symptom indicatives: happy most of the time, happy more than sad or blue, said or blue more than happy, sad or blue most of the time, sad or blue all of the time, so sad I couldn't stand it; the symptom which is sleep and the progressive sequence of symptom indicatives: slept really well and awoke rested, slept all night but woke up tired, awoke but went back to sleep, slept without waking but awoke very early, awoke and couldn't go back to sleep, slept too much; the symptom which is appetite and the progressive sequence of symptom indicatives: ate normally and enjoyed it, ate less but enjoyed it, ate normally but didn't enjoy it, ate less and didn't enjoy it, ate very little, didn't eat anything, ate too much; the symptom which is energy and the progressive sequence of symptom indicatives: great energy, normal energy, less than normal energy, tired easily, drained of energy all day, too tired to move; the symptom which is ability of thick and make decisions and the progressive sequence of symptom indicatives: mentally sharp all day, mentally dull at times, mentally dull but could function, mental dullness interfered with function, could barely function, so mentally dull I couldn't do anything; the symptom which is ability to carry on today and the progressive sequence of symptom indicatives: on top of everything, did as well as most people, tried my best but things went wrong, disappointed in my mistakes, blamed myself for everything wrong, sure things will never improve; the symptom which is enjoyment of the day and the progressive sequence of symptom indicatives: everything was fun, enjoyed most of the day, felt good at least once, tried to stay involved but had little enjoyment, nothing was fun though I tried to stay involved, avoided all people and activities I used to enjoy.

9. The method according to claims 1 or 2 wherein said symptom fields relate to the depression associated symptoms mood, sleep, appetite, energy, thought, guilt/outlook, and enjoyment.

10. A method for treating patients suffering from anxiety by means of the controlled administration of antianxiety medication comprising the steps of:

a. administering to a patient suffering from anxiety, an antianxiety drug on a daily basis for a first dosage period set by the practitioner and in conjunction with the administration of said antianxiety drug during said first dosage period set by the practitioner;

b. administering to said patient suffering from anxiety, a patient-completable symptom chart comprising a plurality of symptom fields, each symptom field corresponding to a particular symptom of anxiety, c. said symptom fields being arranged sequentially on said chart, and d. each of said symptom fieles including a series of printed symptom indicatives, said symptom indicatives each corresponding to a particular degree of a related symptom, and each of said symptom fields including symptom indicatives ranging from an extreme manifestation of the symptom to symptom indicatives indicating improvement in patient condition relative to said extreme symptom, to a positive symptom indicative indicating minimum manifestation of said symptom, e. said symptom indicatives being arranged in said symptom field in a progressive sequence with the indicative relating to said extreme manifestation being at one end of said sequence, symptoms indicating improvements in said patient condition following said extreme symptom in said progressive sequence and said positive symptom being located at the other extremity of said progressive sequence, and f. a patient-markable graph field arranged in association with each of said symptom fields on said patient-completable symptom chart, said graph fields including a series of columns with the number of said columns in said graph field being at least equal to the number of days covered by said first dosage period, and g. each of said columns including zone means for a patient-applied indication, with each of said printed symptom indicatives having a zone means in correspondence therewith in each column of said graph field; and h. said patient assesses his symptoms during said first dosage period by the step of applying an indication in said zone means which corresponds to the symptom indicative most closely corresponding to said patient's assessment of his symptoms on each treatment date over said first dosage period, said patient thereby creating a graphical representation of said patient's symptoms on said symptom chart; and i. wherein upon the completion of said first dosage period, on the basis of said practitioner's assessment of the graph created on said symptom chart by said patient during said first dosage period, said practitioner increases the originally administered dosage of antianxiety drug to be taken by said patient or said practitioner maintains said dosage of antianxiety drug to be taken by said patient at said originally administered dosage level, said dosage of said antianxiety drug being increased when said patient-created graph shows no improvement in said symptoms associated with said patient's anxiety, and the dosage of said antianxiety drug being maintained at said originally administered dosage level when the slope of the line on said patient-markable graph field is upward or shows improvement in said symptoms associated with said patient's anxiety;

j. the administration of said patient-completable chart in combination with said antianxiety drug providing a positive therapeutic effect.

11. The method according to claim 10 wherein said symptom chart further includes a medication schedule field comprising a plurality of columns with each of said columns being associated with date indicia and medication dosage indicia and each of said medication schedule field columns being aligned with the patient-markable graph field columns; and in further association with said medication schedule field columns, a patient-markable zone for receiving an indication of medication self-administered by said patent on said date.

* * * * *

UNITED STATES PATENT AND TRADEMARK OFFICE
CERTIFICATE OF CORRECTION

PATENT NO. : 4,346,697
DATED : August 31, 1982
INVENTOR(S) : Kopel H. Cohen

It is certified that error appears in the above—identified patent and that said Letters Patent is hereby corrected as shown below:

In column 6, line 68, delete "say" and insert --stay--.

Signed and Sealed this

Twelfth Day of April 1983

[SEAL]

Attest:

GERALD J. MOSSINGHOFF

Attesting Officer     Commissioner of Patents and Trademarks